Figure 1:
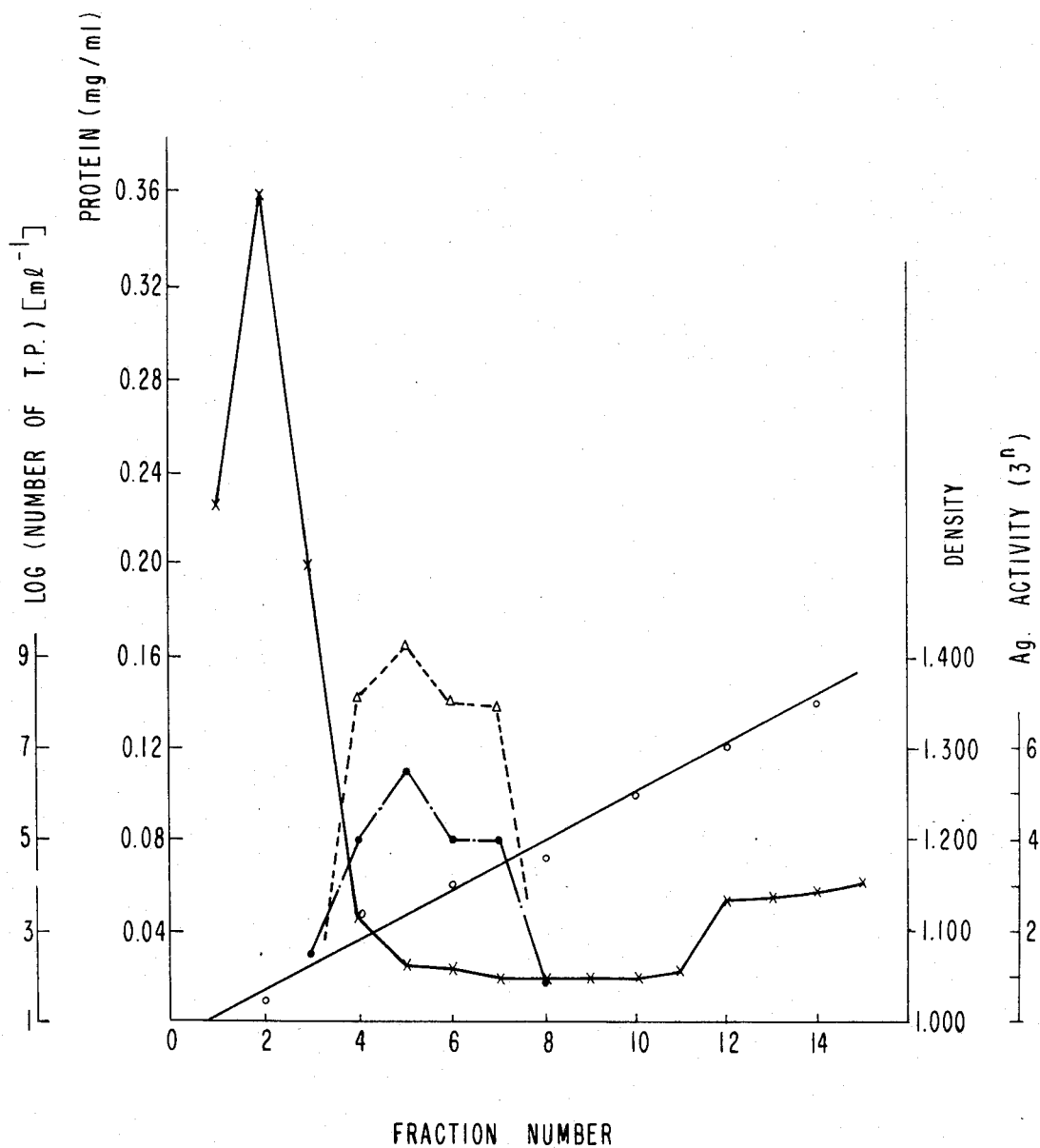

United States Patent [19]

Sato et al.

[11] Patent Number: 4,618,588

[45] Date of Patent: Oct. 21, 1986

[54] REAGENT AND MERCHANDISING KIT FOR USE IN THE DIAGNOSIS OF SYPHILIS AND PREPARATION THEREOF

[75] Inventors: Takashi Sato, Saitama; Emiko Kubo, Tokyo, both of Japan

[73] Assignee: Fujizoki Pharmaceutical Co., Ltd., Tokyo, Japan

[21] Appl. No.: 430,238

[22] Filed: Sep. 30, 1982

[30] Foreign Application Priority Data

Oct. 23, 1981 [JP] Japan ................................. 56-168646

[51] Int. Cl.$^4$ ................ G01N 33/571; G01N 33/555; G01N 33/531; C12Q 1/04
[52] U.S. Cl. ...................................... 436/511; 435/34; 436/520; 436/534; 436/543; 436/811; 436/824; 436/825
[58] Field of Search .............. 436/511, 543, 811, 824, 436/825, 520, 810; 435/34

[56] References Cited

U.S. PATENT DOCUMENTS

| | | | |
|---|---|---|---|
| 2,892,755 | 6/1959 | Portnoy | 436/511 |
| 3,564,089 | 2/1971 | Kiddy | 436/511 |
| 4,123,427 | 10/1978 | Daniel | 436/543 |
| 4,288,426 | 9/1981 | Stevens | 436/511 |

FOREIGN PATENT DOCUMENTS

| | | |
|---|---|---|
| 0038150 | 10/1981 | European Pat. Off. . |
| 2429231 | 1/1975 | Fed. Rep. of Germany ...... 436/511 |
| 1577131 | 10/1980 | United Kingdom . |

OTHER PUBLICATIONS

Tomizawa et al., Usefulness of the Hemagglutination Test Using Treponema Pallidum Antigen (TPHA) for the Serodiagnosis of Syphilis.
European Search Report and Annex to the European Search Report.
Williams, C. A. et al., *Meth. Immunol. and Immunochem.*, vol. II, Academic Press, N.Y., 1968, pp. 81–82, 105–112.

*Primary Examiner*—Sidney Marantz
*Assistant Examiner*—Jeremy Jay
*Attorney, Agent, or Firm*—Burgess, Ryan & Wayne

[57] ABSTRACT

A reagent and merchandizing kit for use in the diagnosis of syphilis by hemagglutination of an anitgen obtained from a culture of pathogenic Treponema pallidum Nichols and which is sensitized on carrier particles in the presence of antibody wherein said antigen is substantially devoid of proteinic fractions of said culture having a specific gravity of less than 1.01, and methods of preparing the same.

8 Claims, 2 Drawing Figures

REAGENT AND MERCHANDISING KIT FOR USE IN THE DIAGNOSIS OF SYPHILIS AND PREPARATION THEREOF

This invention relates to an improved reagent for conducting a Treponema pallidum hemagglutination test (TPHA test) for the diagnosis of syphilis, and a process for producing the same. The TPHA test is carried out by using hemagglutination of antigen which is obtained from a culture of pathogenic Treponema pallidum Nichols (hereinafter referred to as TP) and which is sensitized on carrier particles, such as mammalian red blood cells, in the presence of the corresponding antibody.

More particularly, this invention relates to improving said antigen sensitized on carrier particles capable of detecting the syphilis at the primary stage (hereinafter referred to as primary syphilis).

Prior methods of diagnosing syphilis, included the STS method which was insufficient in specificity. Accordingly, various methods utilizing the antigen-antibody reaction between the antigen of TP cells and the antibody in the blood serum of a patient have been developed. For instance, the FTA test provides for the reaction of the antibody in the serum of a patient with the antigen of TP cells, and the antibody which is the product of the above antigen-antibody reaction is detected by using the anti gamma globulin which is labelled with a fluorescent material. This FTA test is disadvantageous because it is a complicated procedure.

On the other hand, the TPHA test which was developed by T. Tomizawa et al., is widely employed because of its sensitivity, specificity, and simple procedure. Presently, this TPHA test is used to diagnosis syphilis but has not been successfully used to detect primary syphilis occurring in patients infected with syphilis for 2 or 3 months. The conventional test often provides a negative test. Accordingly, in order to detect primary syphilis, it is necessary to employ the STS method together with the TPHA test.

It has now been found that in the case of the antigen sensitized on a carrier for the measurement of immunoglobulin using indirect passive hemagglutination such as the TPHA test, when a particular impurity is removed from a mixture containing antigen prior to sensitization on carrier particles, the resulting antigen sensitized on a carrier is able to detect primary syphilis. As to the conventional antigen sensitized on a carrier, proteinic impurities of more than 90% are derived from the testis of rabbit in which the TP is cultured. According to the present invention, among these proteinic impurities, the fractions having a specific gravity of less than 1.01 are removed prior to sensitization of the antigen.

The solution of antigen for sensitization may be obtained according to the conventional method. Namely, as to the TP strain for inoculation, the strain of WHO pathogenic standard Nichols or the strain employed for TPHA test in each organization where syphilis test is carried out may be employed. The WHO pathogenic standard Treponema pallidum Nichols strain is available, for instance, from CDC (Center for Disease Control, Public Health Service, U.S. Department of Health, Education and Welfare, Atlanta, Ga.). Rabbits are inoculated with TP in the testis and housed for 11 to 14 days. After the cultivation, multiplied cells are collected according to the method of Miller et al. (Miller et al., Journal of Immunology, Vol. 96, p. 450 (1966)).

After cultivation, the testis is minced, and multiplied cells are extracted from the minced testis by using the mixed solution consisting of equal volume of inactivated normal serum of rabbit and 1/7 M saline solution. The extracts are sufficiently centrifuged at $200 \times g$ for 10 minutes, and the precipitates of large particles (tissues of testis) are removed. The supernatant is centrifuged again at $19,000 \times g$ for 90 minutes, and the precipitations containing the multiplied cells are recovered. Then, the precipitates are washed three times with chilled 0.075 M sodium oxalate.

In the conventional method, the washed precipitates are suspended in a suitable buffer solution, and the microbial cells of the TP are destroyed by treatment with a homogenizer or by sonication. The solution containing the destroyed cells is employed as the solution of antigen to be sensitized on the carrier particles.

According to the present invention, the fractions having specific gravities less than 1.01 are removed from the above solution of antigen prior to the sensitization on the carrier particles.

The removal of these fractions may be carried out according to known fractionation methods such as density gradient, gel filtration, ultracentrifugation, ultrafiltration, fractionation using ammonium sulfate, and electrophoresis. Among these, density gradient and ultracentrifugation are most suitable for use in the present invention. The removal of the above fractions may also be carried out by adsorption of the antigen on the corresponding antibody which is immobilized on a carrier.

The present invention is based on the discovery that the low sensitivity of the conventional TPHA test against the primary antibody (Ig-M) compared to the sensitivity against the antibody (Ig-G) is caused by the particular impurities contained in the extracts of the TP. Accordingly, the above-mentioned particular impurities which are contained in the fractions having a specific gravity of less than 1.01 need not be removed completely. It is sufficient that they are removed until the remaining impurities do not substantially interfere with the antigen-antibody reaction between the antigen sensitized carrier and the Ig-M antibody of syphilis. The removal may be carried out either before or after the destruction of the microbial cells. However, the removal is preferably carried out before the destruction of the microbial cells by the density gradient method.

According to the present invention, it is necessary to remove the proteinic impurities having a specific gravity less than 1.01, and preferably less than 1.05. The fractions having a specific gravity greater than 1.20 are also preferably removed.

The protein content of the antigen solution for sensitization which is obtained from the testis of rabbit in the conventional manner is greater than 0.6 mg per $10^9$ TP cells, whereas the antigen solution for sensitization employed in the present invention is less than 0.3 mg per $10^9$ TP cells, and usually less than 0.1 mg per $10^9$ TP cells. The protein content mentioned above was measured by Lowry's method (Lowry et al., Biol. Chem., Vol. 193, pp 265–275 (1951)), and the number of TP cells was determined by direct counting of TP cells in the sample placed on a bacteria counter (manufactured by C.A. Hauser & Son) using a dark-field microscope.

The destruction of TP cells may be carried out in a conventional manner during preparation of reagent for TPHA test, and, for example, by treatment with a homogenizer, by sonication, by treatment with surfactant or an enzyme, by autolysis, and by freezing and thawing. When the removal of the particular impurities previously described is carried out prior to the destruction of TP cells, the fractions of TP cells from which the particular impurities are removed are preferably washed with a buffer solution by means of centrifugation and then the TP cells are destroyed.

The suspension of the destroyed cells is diluted with a buffer solution, if necessary, and then, antigen in the suspension is sensitized on carrier particles, such as sheep red blood cells, in a conventional manner.

The carrier particles employed in the present invention are not limited to sheep red blood cells, and include any particles usable as a carrier of indirect passive hemagglutination using an antigen-antibody reaction, such as various mammalian erythrocytes, microbial cells, polystyrene latex, and gelatin particles.

The antigen sensitized carrier which may be lyophilized is combined with other conventional reagents for use in the diagnosis of syphilis, such as a standard serum, an unsensitized carrier, an absorbing solution, a diluent, a reconstituting solution, etc. to obtain a complete reagent for use in the diagnosis of syphilis.

In the antigen sensitized carrier of the present invention, non-specific reactions are slightly increased. However, when the solution containing the antigen derived from the strain belonging to the genus Treponema which lives in humans and animals is employed as one of the above reagents, such as the absorbing solution, the diluent and the reconstituting solution, these non-specific reactions can substantially be eliminated. Examples of such strains include *Treponema denticola*, *Treponema mucosum*, *Treponema orale*, *Treponema scoliodontum*, *Treponema vincentii*, *Treponema macrodentium*, *Treponema trimerontium*, *Treponema buccalis*, *Treponema enterogyratum*, *Treponema paraluis-cuniculi*, *Treponema hyos*, and *Treponema penortha*.

The solution containing the above mentioned antigen may be produced in a conventional manner used for producing the reagent for the TPHA test. For example, a culture broth of the strain is centrifuged at $10,000 \times g$, and the supernatant is separated. The supernatant is heated to 100° C., and deposits are removed to obtain a culture filtrate. The precipitates resulting from the centrifugation step are added to the culture filtrate to obtain a solution containing the above antigen. In this case, the cells of the strain may be destroyed by treatment with a homogenizer or by sonication.

The antigen sensitized carrier of the present invention provides a sensitive and stable technique for the detection of late syphilis and primary syphilis in patients infected within one month. This antigen sensitized carrier provides for the easy diagnosis of syphilis by eliminating the necessity of using the STS method.

The present invention is further illustrated by the following examples which are not meant to limit the scope of the invention as previously described.

EXAMPLE 1

The strain of WHO pathogenic standard *Treponema pallidum* Nichols, obtained from the National Institute of Health, Ministry of Health & Welfare (Japan) was cultured, and the multiplied cells were suspended at a concentration of $6.0 \times 10^7$ cells/ml.

One ml of the suspension was inoculated in each testis of 10 rabbits, and cultured for 12 days. The testes were excised from each rabbit and minced. Multiplied cells were extracted from the minced testes by using 1000ml of the mixed solution consisting of an equal volume of inactivated normal serum of rabbit and 1/7 M saline solution.

The extracts were centrifuged at $200 \times g$ for 10 minutes, and the precipitates were removed. The supernatant was centrifuged again at $19,000 \times g$ for 90 minutes, to thereby precipitate the TP cells.

The precipitates containing the TP cells were washed three times with chilled 0.075 M sodium oxalate, and were suspended in 10 ml of 1/15 M phosphate buffer solution having a pH of 6.4. The number of TP cells in the suspension was counted, and then the suspension was diluted so that the concentration of the TP cells was $2 \times 10^9$/ml to obtain a crude TP antigen solution.

A density gradient of sodium diatrizoate solutions which consisted of 60%, 37.5%, 25.0% and 19.0% (w/v %) was prepared in a 15ml cellulose tube, and one ml of the crude TP antigen solution was layered on the topmost layer of the sodium diatrizoate solution. The cellulose tube was centrifuged at 25,000 rpm ($76,000 \times g$) at 20° C. for 2 hours, and 15 one ml fractions were successively withdrawn from the top of the layers.

The number of TP cells and the protein concentration of the crude TP antigen solution, and the number of TP cells (triangle), the density (open circle), the protein concentration (saltire) and the antigenic activity of the TP cells (closed circle) in each of the above fractions were measured, and the results are shown in FIG. 1.

Each value was shown as follows:

The number of TP cells was determined by direct counting of TP cells in each sample placed on a bacteria counter (manufactured by C.A. Hauser & Son) using a dark-field microscope.

The density was determined by weighing each 100 μl of sample.

The protein concentration was determined by the Lowry method. Namely, sodium carbonate solution containing sodium potassium tartrate and copper sulfate was added to each sample, and the mixture was allowed to stand for 10 minutes at room temperature. Then, Folin's reagent was added to the mixture, and after more than 30 minutes, the mixture was colorimetrically determined at 750 nm.

As to the antigenic activity of TP, each sample was sonicated in order to destroy the TP cells. Then, 25 μl of the sonicated sample was placed in the left end well of a micro titer plate, and diluted twice by twice with the solution of antibody against TP antigen on the micro titer plate. The micro titer plate was kept at 37° C. for 30 minutes, and the antigen sensitized carrier was added to each well. The antigenic activity of TP is the dilution ratio when hemagglutination appears.

The fractions of Nos. 4 to 7 in FIG. 1 were combined to obtain one ml of the antigen solution for sensitization. The number of TP cells in this antigen solution was $1.91 \times 10^9$, and the protein content was 0.116 mg. On the other hand, the number of TP cells in the crude TP antigen solution was $2.0 \times 10^9$, and the protein content was 1.213 mg.

Using this antigen solution for sensitization, the antigen was sensitized on sheep red blood cells, and the sensitized cells were lyophilized.

Using this lyophilized matter and an antigen sensitized carrier which was prepared from the crude TP antigen solution in a conventional manner, the diagnoses of syphilis were carried out. The samples employed were three serums ($G_1$, $G_2$, $G_3$) obtained from the patients having syphilis who were sufficiently treated and three serums ($M_1$, $M_2$, $M_3$) obtained from the patients having primary syphilis infected after 3 to 4 weeks. The former three serums contained only Ig-G antibody, and the latter three serums contained only Ig-M antibody as confirmed by gel filtration.

The results are shown in Table 1.

TABLE 1

|  | Primary Syphilis | | | Late Syphilis | | |
| --- | --- | --- | --- | --- | --- | --- |
|  | $M_1$ | $M_2$ | $M_3$ | $G_1$ | $G_2$ | $G_3$ |
| The Product of the Invention | + (×320) | + (×320) | + (×160) | + (×640) | + (×320) | + (×160) |
| The Conventional Product | − (×40) | − (×40) | − (×20) | + (×2560) | + (×640) | + (×320) |

Figures in parentheses indicate antibody titer. Positive means antibody titer greater than 80.

EXAMPLE 2

Figure 2:
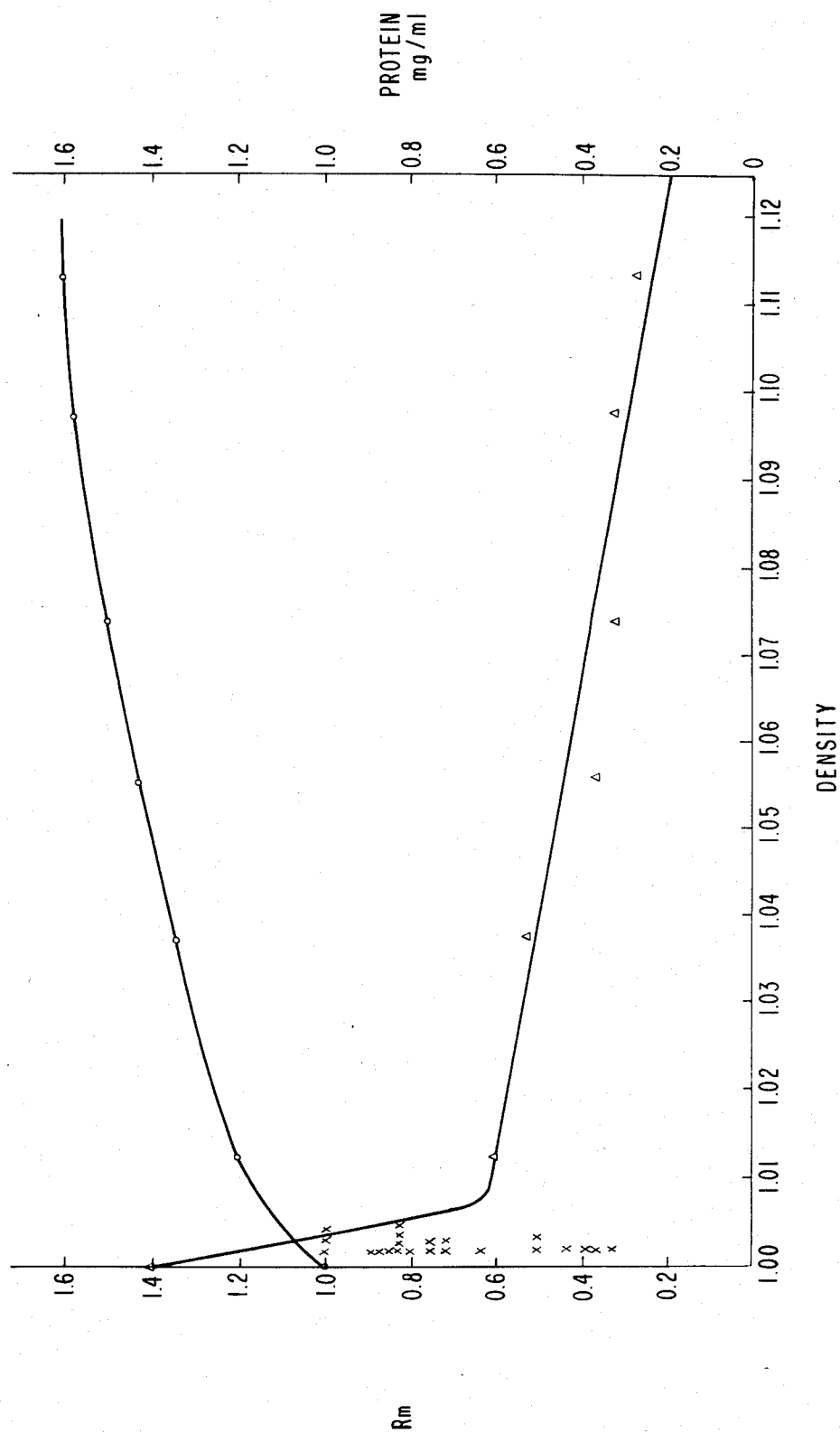

25% Sodium diatrizoate solutions (d=1.161) were placed in centrifuge tubes, and the sodium diatrizoate solutions having the specific gravities shown in FIG. 2 were layered thereupon.

The crude TP antigen solution obtained in Example 1 was layered on each upper layer, and each tube was centrifuged. The middle fraction formed between the two sodium diatrizoate solutions was withdrawn.

The protein concentration of each middle fraction was measured by Lowry's method. Each middle fraction was sensitized on sheep red blood cells in a conventional tannic acid method, and the titers of the antigen sensitized sheep cells were measured according to the TPHA test by using serum containing only Ig-M antibody and serum containing only Ig-G antibody. Both serums were previously adjusted by mixing the serums of several syphilis patients to show equal titers when the TPHA test was carried out using the antigen sensitized sheep cells prepared by sensitizing the crude TP antigen solution on sheep red blood cells.

The results are shown in FIG. 2. The abscissa indicates the specific gravity of the sodium diatrizoate solution of the upper layer, and the left ordinate indicates the ratio ($R_M$) of the titer of the antigen sensitized sheep cells against Ig-M antibody/the titer against Ig-G antibody. The right ordinate indicates the concentration of protein, and circles represent $R_M$ and triangles represent the concentration of protein.

As can be seen from FIG. 2, the sensitivity of the antigen sensitized sheep cells against Ig-M antibody of syphilis increases considerably more than that against Ig-G antibody of syphilis by the removal of the fractions having lower specific gravities, particularly the fractions having a specific gravity less than 1.01.

The TPHA test was carried out several times on the above serums. The results are shown by (X) on the left ordinate of FIG. 2.

In order to illustrate the effect of the solution containing the antigen derived from the strain belonging to genus the Treponema, following experiment was carried out.

Experiment 20 ml of the culture broth containing Treponema mucosum E-21 obtained from Nippon Dental University in concentration of $1.4 \times 10^8$ cells/m was centrifuged at 10,000×g at 4° C. for 30 minutes, and the precipitates containing microbial cells were separated from the supernatant. The supernatant was heated for 30 minutes in a water bath at 100° C. After cooling, the supernatant was filtered using Whatman No. 2 filter paper, and the culture filtrate was obtained.

The above precipitates were suspended in a solution designated as A - solution containing:

| | |
| --- | --- |
| $Na_2HPO_4.12H_2O$ | 20.7 g/l |
| $KH_2PO_4$ | 2.3 g/l |
| NaCl | 4.3 g/l |
| Arabic gum | 2.5 g/l |
| $NaN_3$ | 1.0 g/l |
| Healthy rabbit serum | 10 ml/l |
| 10% Tween 80 | 1 ml/l |

The suspension was sonicated at a frequency of 20 kHz for 10 minutes to thereby destroy the microbial cells. The sonicated suspension was mixed with the culture filtrate, and total volume of the mixture was adjusted to 40 ml by using the above solution. The mixture was designated E-solution.

On the other hand, 20 ml of the culture broth containing Treponema denticola S-173 obtained from Nippon Dental University in concentration of $1.4 \times 10^8$ cells/ml was treated in the same manner as the case of Treponema mucosum E-21, and 40 ml of the mixture was obtained and designated S-solution.

The E-solution and the S-solution were each diluted 10 times with the A-solution, and the diluted solutions were mixed with each other. The diluted mixture so produced was designated ES-solution.

0.06 Gram of wet cells of Treponema phagedenis Reiter was added to 1 l of the A-solution, and the mixture was designated B-solution.

Both the E-solution and the S-solution were diluted 10 times with the B-solution, and the diluted solutions were mixed with each other. The mixture was named BES-solution.

Using the lyophilized antigen sensitized on sheep cells which was obtained in Example 1, and one of the above ES-, BES-, and B-solutions, the TPHA test was carried out. In this test, the above solution was employed as the diluent, the reconstituting solution, and the absorbing solution. 560 Serums of healthy persons were diluted 10 times with the above solution, and the diluted serums were employed as the samples.

The results of the TPHA test are shown in Table 2.

TABLE 2

|  | The number of persons detected as positive (%) |
| --- | --- |
| ES-solution | 10 (1.8%) |
| BES-solution | 2 (0.36%) |
| B-solution (control) | 50 (8.9%) |

We claim:

1. In a regent for use in the diagnosis of syphilis by hemagglutination of an antigen obtained from a cultrure of pathogenic Treponema pallidum Nichols and wherein carrier particles are sensitized with said antigen, the improvement which comprises said antigen being subtantially devoid of proteinic fractions of said culture, said proteinic fractions having a specific gravity less than 1.01.

2. The reagent of claim 1, wherein said antigen is substantially devoid of said proteininc fractions having a specific gravity of less than 1.05.

3. The reagent of claim 1 or 2, wherein said antigen is substantially devoid of said proteinic fractions having a specific gravity greater than 1.20.

4. The reagent of claim 1, wherein said carrier particles are selected from the group consisting of mammalian erythrocytes, microbial cells, polystyrene latex particles and gelatin particles.

5. The reagent of claim 4, wherein said carrier particles are sheep red blood cells.

6. A process for producing the reagent of claim 1, comprising substantially removing proteinic fractions of said culture, said proteinic fractions having a specific gravity of less than 1.01 and sensitizing carrier particles with said antigen.

7. The process of claim 6, further comprising removing said proteinic fractions by the separation of same in a density gradient.

8. The reagent of claim 4 wherein the mammalian erythrocytes are sheep red blood cells.

* * * * *